United States Patent [19]

Hemer

[11] Patent Number: 5,019,080
[45] Date of Patent: May 28, 1991

[54] DRIVE SYSTEM FOR PROSTHETIC FASTENERS

[75] Inventor: H. Michael Hemer, Rockford, Ill.

[73] Assignee: Trextron Inc., Providence, R.I.

[21] Appl. No.: 479,514

[22] Filed: Feb. 13, 1990

[51] Int. Cl.$^5$ .................... A61F 5/04; F16B 23/00
[52] U.S. Cl. ................................ 606/73; 411/402; 411/403; 606/104
[58] Field of Search ................................ 606/72-74, 606/104; 411/402-405, 408, 410, 395, 919

[56] References Cited

U.S. PATENT DOCUMENTS

| | | | |
|---|---|---|---|
| 2,083,092 | 6/1937 | Richer | 411/403 |
| 2,969,250 | 1/1961 | Kull | 411/403 |
| 3,584,667 | 6/1971 | Reiland | 411/402 |
| 4,269,246 | 5/1981 | Larson et al. | 411/403 |
| 4,459,074 | 7/1984 | Capuano | 411/403 |

OTHER PUBLICATIONS

Line Head System, Inc., Fastening System Brochure, date approximately 1990, General Reference.
Snap-On Medical Products, "Captive Twist" Information Sheet, Date approximately 1990, General Reference.

Primary Examiner—Stephen C. Pellegrino
Assistant Examiner—Gary Jackson
Attorney, Agent, or Firm—R. A. Giangiorgi

[57] ABSTRACT

A fastener and fastener driver system for prosthetic devices and other more common type usages. The fastener is threaded with a driver engaging socket formed in the fastener head. The driver imparts rotational torque to the fastener and includes a drive bit portion engagable with the driver engaging socket formed in the fastener. The driver engaging socket and drive bit are formed with cooperative hexalobular surfaces the sides of which are generally parallel for releasably retaining the fastener on the driver. Each convex curved surface of the hexalobular surface formed on the end of the driver bit is downwardly inwardly beveled. Three alternating concave curved surfaces in the socket are formed with cooperatively mating beveled surface portions. When the driver is engaged with a fastener the beveled surface portions of the socket are triangularly engaged by the driver to securely releasably retain the fastener on the driver to prevent wobbling of the fastener when driven by the driver.

12 Claims, 2 Drawing Sheets

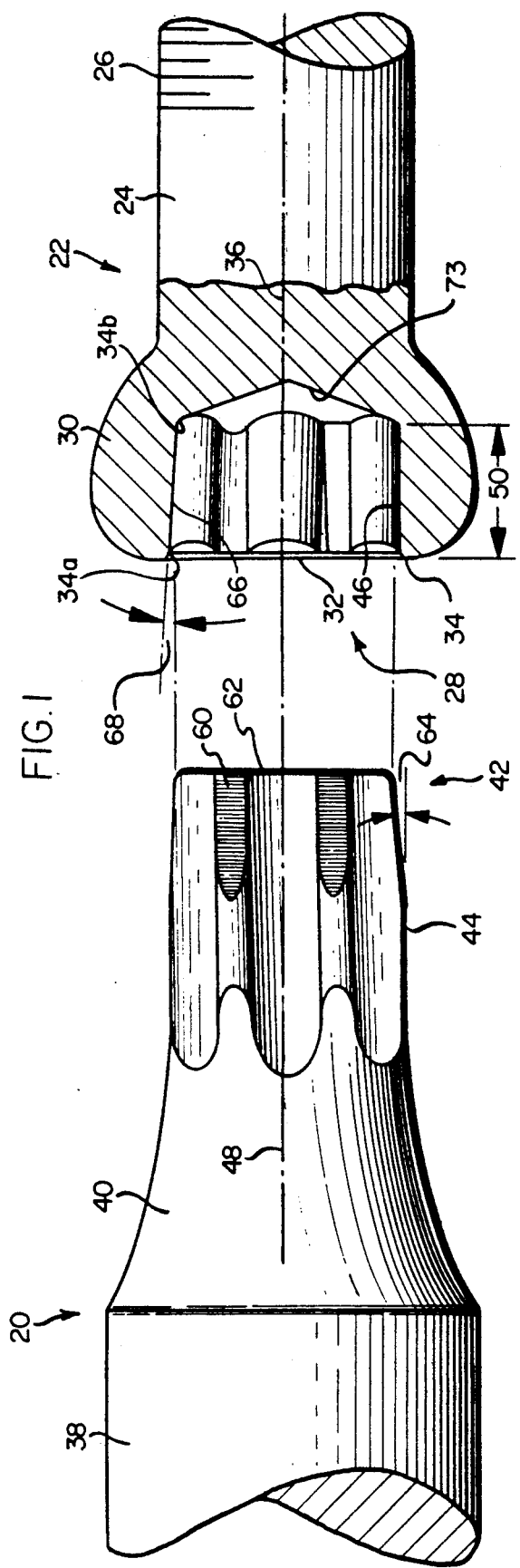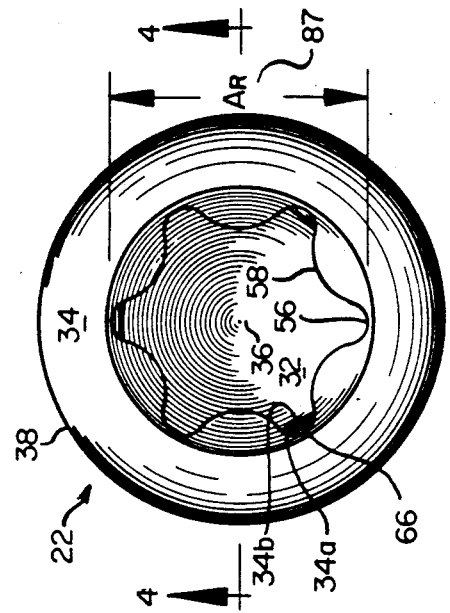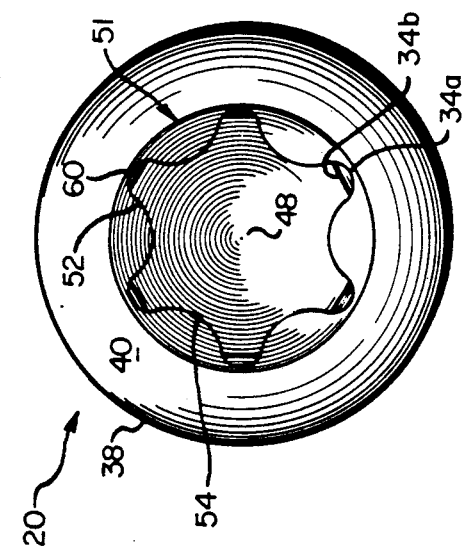

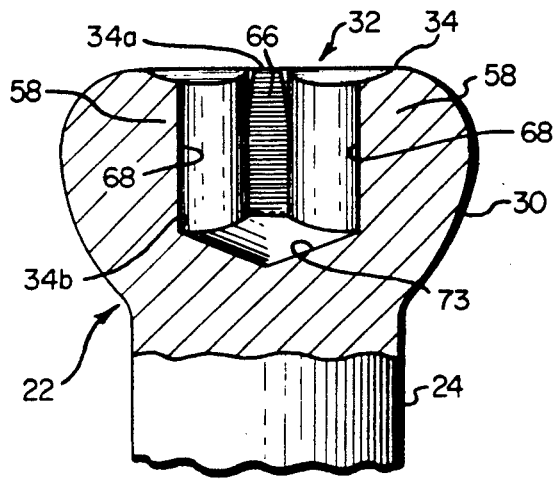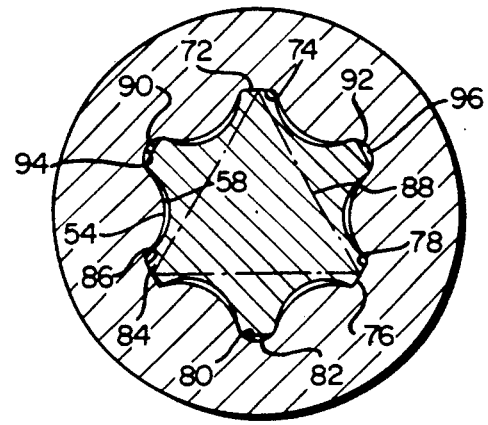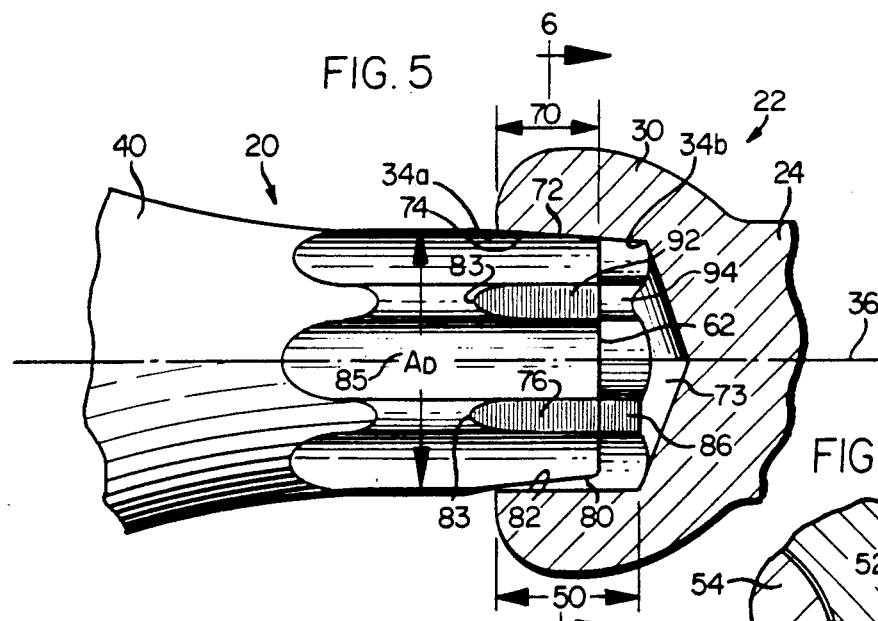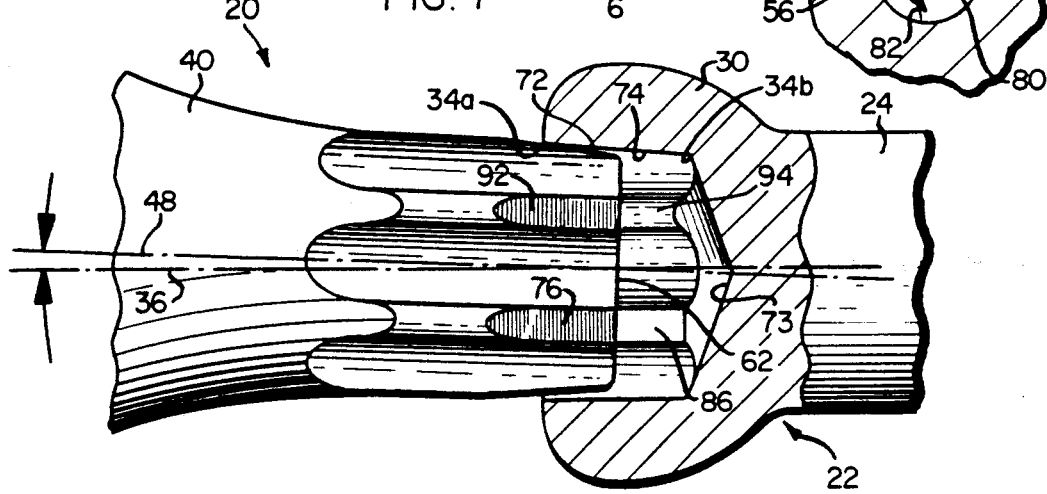

DRIVE SYSTEM FOR PROSTHETIC FASTENERS

BACKGROUND OF THE INVENTION

This invention relates generally to the fastener arts and more particularly to a fastener drive system. Still more particularly, the invention relates to a fastener drive system for applications where it is desirable that the fastener be maintained on the end of the drive tool in a co-axial, wobble free orientation, such as in the attachment of a medical prosthesis to bone and other more common type usages.

Medical prosthetic arts have advanced substantially in both design and the materials used creating in prosthetics. Typically, a combination of mechanical fasteners and adhesives are used to secure a prosthesis to surrounding bone. A high degree of precision is required in order to securely retain the prosthesis in a proper working position. When the prosthesis is fitted to surrounding bone it is preferred to make the prosthesis fit correctly the first time to avoid having to make adjustments. As such, it is advantageous to drive fasteners used to secure the prosthesis correctly on the first attempt to provide secure attachment and to avoid unnecessary mounting and remounting of the prosthesis.

Surgeons performing prosthetic installation operations work under most difficult operating conditions. Not only must the surgeon focus his attention on the operating site and any complications which may arise, the operating area is not usually freely accessible creating difficulty in fitting and positioning the prosthesis. Therefore, while attaching the prosthesis the surgeon requires one hand to expose and hold the prosthesis in position leaving only one hand free to drive fasteners. Clearly, fasteners and fastener drive systems used in securing the prosthesis to bone require single-handed operation. It is necessary that the fastener used in such an operation be retained by the driver so that the surgeon can position the fastener and drive it into secure engagement using one hand.

In retaining a fastener on a driver, an easily releasable securely retaining friction fit is preferred. Prior art fastener retaining systems have employed magnetic retainers which although capable of retaining a fastener on the end of the drive tool gives rise to other problems. Primarily, the fastener is not retained securely enough such that when a side force contacts the fastener it comes loose from the driver.

Other prior art fastener retaining systems utilized retaining mechanisms which held a fastener in place through an arrangement of arms or fingers. These retaining mechanisms, however, could interfere with the operation and require additional space within the operation sight for releasing the fastener. Further, the mechanical retaining mechanisms had problems in suppressing fastener wobble as the fastener was driven. The type of engagement between the fastener and the driver is very important since prior art fastener drive systems are clearly inferior for this extremely critical high precision medical application. For example, many prior art systems have problems with "camout", which forces the driver out of the fastener recess, potentially reaming the fastener recess and damaging the driver and operating site. Camout occurs when drive torque is applied to the inclined walls of typical prior art fasteners such as cruciform or phillips type drive recesses. While, in certain situations camout can be overcome by increasing the end load on the driver to more securely force it into the recess, additional end load can create damage in medical procedures. For example, when applying additional end load, should the driver camout of the fastener, the driver may slip into the operating sight and gore tissue, damage bone or damage the prosthesis. Clearly for medical applications, a better alternative must be provided.

As an additional requirement for a fastener in a prosthesis installation application, the fastener must be correctly driven on the first attempt. Correctly driving the fastener on the first attempt provides secure retention of the prosthesis to the bone. The fastener must be able to hold the prosthesis to the bone for the life of the patient and therefore loose fasteners cannot be tolerated. Clearly, if the fastener has to be removed and reinserted for proper seating or because the fastener wobbled while being driven and seated at an angle, an eccentric hole would be created and potentially result in a loose fitting prosthesis.

Prior art mechanisms which securely retain the fastener to the driver have problems with the fastener wobbling about the central axis extending through the fastener and the driver. Typically, the fastener has a recess formed on a top surface of the head and the driver has a cooperatively mating male protrusion which is formed to engage the recess in the fastener. An example of such a fastener and driver combination is the standard hexalobular TORX fastener and corresponding driver. The standard TORX fastener employs a driver bit which, in cross section, has six equidimensioned and equispaced curved lobes which engage in corresponding cross-sectional shaped recesses in the head of the fastener. The sides of the standard TORX fastener are generally parallel to the central axis. While the standard TORX fastener is retainable on the corresponding driver, it has a degree of wobble and is not sufficiently securely retained on the driver for medical applications.

Prior art prosthesis fasteners have attempted to overcome both the problem of retention on the driver to permit a single-handed operation and wobble prevention. One prior art device attempts to overcome these problems by forming the driver bit in a hexalobular form with a spiral twist to the lobes relative to the central axis of the bit. This fastener, while reducing wobble and securely retaining the fastener on the driver has the problem in that the fastener is retained too securely. While the secure retention of the fastener helps in positioning the fastener in the operating sight, the spiral twist makes it difficult to disengage the driver from the fastener. Further, since the spiral in the drive recess follows the thread spiral, the fastener may actually be loosened upon disengaging the driver.

Additionally, the degree of retaining force between the fastener and the driver bit of this prior art system results in shortening the driver life. It is important that the driver is not the critical component in the driver system such that even after some wear causing use the driver can be used to satisfactorily complete an operation should other drive bits be unavailable or damaged. As such, it is preferred that the fastener be prevented from wobbling even after the driver bit has developed a degree of wear.

The present invention, as will be detailed more fully hereinafter, overcomes the above-described problems. More specifically, the present invention provides a fastener drive system which securely retains a fastener on a driver bit, prevents wobbling of the fastener during driving and permits the driver to be easily removed from the fastener once the fastener is installed or seated.

OBJECTS AND SUMMARY OF THE INVENTION

A general object of the present invention is to provide a fastener which is securely retainable on a driver.

Another object of the present invention is to provide a fastener which is securely retainable on a driver and which prevents wobble of the fastener relative to a central axis of the fastener and driver bit.

A more specific object of this invention is to provide a fastener and driver system which permits the driver to be easily removed from the fastener once the fastener is installed.

In accordance with the foregoing, the present invention concerns a drive system which comprises a fastener and fastener driver. The fastener is threaded and provided with a driver engaging socket formed in the fastener head. The driver imparts rotational torque to the fastener and includes a drive bit portion engagable in the socket formed in the fastener. The driver engaging socket and drive bit are formed with cooperative hexalobular surfaces the sides of which are generally parallel for releasably retaining the fastener on the driver. Each outwardly curved surface of the hexalobular surface formed on the end of the driver bit is downwardly inwardly beveled. Three alternating inwardly curved surfaces in the socket are formed with cooperatively mating beveled surfaces. When the driver is engaged with a fastener the beveled surfaces of the socket are triangularly engaged by the driver to securely releasably retain the fastener on the driver to prevent wobbling of the fastener when driven by the driver.

BRIEF DESCRIPTION OF THE DRAWINGS

The organization and manner of operation of the invention, together with the further objects and advantages thereof, may best be understood by reference to the following description taken in connection with the accompanying drawings in which like reference numerals identify like elements in which:

FIG. 1 is a partial fragmentary side view of a driver bit positioned for insertion into a fastener socket formed in an end surface of a fastener;

FIG. 2 is an end view of the driver bit as shown in FIG. 1;

FIG. 3 is an end providing an axial view the recess of the socket as illustrated in FIG. 1;

FIG. 4 is a partial sectional side view of the socket formed in the end surface of the fastener taken along line 4—4 as illustrated in FIG. 3;

FIG. 5 is an enlarged partial sectional side view of the driver and socket as illustrated in FIG. 1 in which the driver is insertably engaged with the socket;

FIG. 6 is an enlarged cross-sectional view of the driver insertably engaged with the socket taken along the line 6—6 of FIG. 5 showing triangularized engagement of alternately spaced beveled surfaces formed in the socket with the beveled surfaces of the drive bit;

FIG. 7 is a partial fragmentary side view illustrating the removal of the driver bit from the fastener socket; and FIG. 8 is an enlarged detail of one of the driver bit lobes positioned in a non-beveled fastener socket flute.

It should be noted that the dimensional relationships between the members of the illustrated embodiment may vary in practice and may have been varied in the illustrations to emphasize certain features of the invention.

DETAILED DESCRIPTION OF THE ILLUSTRATED EMBODIMENT

While this invention may be susceptible to embodiment in different forms, there is shown in the drawings and will be herein described in detail, one specific embodiment with the understanding that the present disclosure is to be considered an exemplification of the principles of the invention, and is not intended to limit the invention to the embodiment illustrated.

FIG. 1 provides a partial fragmentary side view of a drive tool 20 positioned for engagement with a fastener 22. The fastener 22 is formed with a shank 24, one end of which is formed with threads 26 and the opposite end of which is formed with tool engaging means 28. Tool engaging means 28 are formed on a slightly enlarged head portion 30 of the shank 24 and include a recessed socket 32 formed in an end surface 34 having a top edge 34a and a bottom edge 34b, a central axis 36 extends longitudinally through the shank 24 and correspondingly the center of the recessed socket 32.

The drive tool 20, as shown in FIG. 1, includes a drive tool shank 38 which tapers along the shank taper 40 to a bit portion or tip 42. As described in greater detail in FIG. 2, the bit tip 42 has an outer surface 44 which cooperatively engages an inner surface 46 of the recessed socket 32. Further, a bit axis 48 is coincident with the central axis 36 of the fastener 22 when the bit tip 42 is engaged with the recessed socket 32.

Engagement of the drive tool 20 with the fastener 22 permits the fastener 22 to be rotationally driven by the drive tool 20 which applies a rotational torque to the fastener 22. The depth 50 of the recessed socket 32 is dimensioned to sufficiently accommodate a portion of the bit tip 42 necessary for proper driving engagement as will be discussed further hereinbelow.

An end view of the drive tool 20 as shown in FIG. 1 is illustrated in FIG. 2. FIG. 2 shows the alternating concave and convex generally partially cylindrical surfaces which engage correspondingly formed surfaces in the recessed socket 32 (see FIG. 3). This type of drive engagement shape is known as a hexalobular shape. The convex generally partially-cylindrical surfaces or bit lobes 52 smoothly merge with concave generally partially-cylindrical surfaces or bit flutes 54. Each bit lobe 52 as well as each bit flute 54 are identical, within practical tolerances, to the other bit lobes 52 and bit flutes 54 in the configuration. Sizes and dimensions of the bit lobes 52 and bit flutes 54 may vary among designs, however, the six bit lobes 52 as illustrated in the preferred embodiment are equally spaced apart by the bit flutes 54.

Referring to FIG. 3, the end view of the socket 32 reveals that a corresponding shape has been formed in the recessed socket 32 on the end surface 34 for receiving the hexalobularly shaped 51 bit tip 42. The bit lobes 52 are axially insertable into recess flutes 56 while the bit flutes 54 engage a corresponding recess lobe 58. While a male drive tool 20 and female recessed socket 32 are illustrated in the present embodiment the relationship between these engageable surfaces could be reversed with a drive tool 20 formed with the tool engaging means 28 and the fastener 22 formed with the male bit tip 42.

As shown in FIGS. 1, 2 and 3 the bit lobes 52 of the bit tip 42 are formed with a beveled portion 60 which tapers towards a tip 62 at approximately 3.5° angle 64.

Generally, the beveled portion 60 formed on each bit lobe 52 is a planer bevel, however, a curved taper may be formed angling inwardly towards the tip 62. These beveled surfaces 60 are also shown in FIG. 2 as viewed from the tip 62 towards the drive tool shank 38. The recessed socket 32 has correspondingly formed flute beveled portions 66 which slope towards the central axis 36 from the top edge 34a to the bottom edge 34b. However, the flute beveled portions 66 are only formed on alternating recess flutes 56. Therefore, in the hexalobular shaped recessed socket 32 three non-neighboring recess flutes 56 are not beveled and three non-neighboring recess flutes 56 are formed with flute beveled portions 66. The flute beveled portions 66 taper from the end surface 34 inwardly towards the central axis 36 at an angle 68 of approximately 3.5°.

FIG. 4 provides a partial sectional side view of the recessed socket 32 formed in the end surface 34 of the fastener 22 taken along 4—4 as illustrated in FIG. 3. This view of the recessed socket shows a front view of a flute beveled portion 66. Additionally, this cross-section is taken through opposed recess lobes 58 and shows lobe crests 68.

FIG. 5 illustrates the drive tool 20 engaged with the recessed socket 32. The drive tool 20 is engaged in the recessed socket 32 to a depth as noted by measurement 70 which is less than the total depth 50 of the recessed socket to prevent the tip 62 from "bottoming out" in the bottom 73 of the recessed socket 32. Engagement occurs when three of the six beveled surfaces 60 formed on the drive tool 20 engage the three flute beveled portions 66 of the recessed socket 32. As shown in FIG. 5, beveled portion 72 is engaged with flute beveled portion 74. Similarly, drive tool beveled portion 76 is engaged with flute beveled portion 78 (see FIG. 6). It should be noted that tool beveled portion 80 is not in engagement with non-beveled flute 82. Bottoming out is further prevented since the area above the bevel tips 83 has a dimension indicated by $A_D$ 85 which is greater than a corresponding dimension indicated by $A_R$ 87 as shown in FIG. 4.

FIG. 6 provides an enlarged cross-sectional view of the drive tool 20 inserted in the recessed socket 32 as taken along 6—6 in FIG. 5 thereby providing greater detail with regard to the relationship and function of the engagement surfaces. As shown in FIG. 6, tool beveled portions 72, 76, 84 are engaged with flute beveled portion 74, 78, 86, respectively. These engaged beveled portions create triangularized engagement as illustrated by the dashed line triangle 88. Further, tool beveled portions 80, 90, 92 are not in engagement with flutes 82, 94, 96 which are not beveled.

Triangularized engagement promotes three pointed self-centering of the drive tool 20 in the recessed socket 32 thereby minimizing wobbling of the tool 20 in the socket 32 while the fastener 22 is driven. Typically if all six bit lobes 52 of the hexalobular portion engaged all six recess flutes 56 two bit lobes 52 would dominate the engagement making the engagement unbalanced and cause wobbling. Since alternating flutes 82, 94, 96 are not beveled, the corresponding beveled tool portions 80, 90, 92 do not engage the corresponding flutes thereby promoting triangularized engagement 88. FIG. 8 provides an enlarged detail of the position of the tool beveled portion 80 in relation to the flute 82 clearly showing that the beveled portion 80 does not engage the unbeveled flute 82.

When the tool 20 is inserted into the socket 32 the respective tool beveled portions 72, 76, 84 engage the corresponding recess beveled portions 74, 78, 86. Application of a small compressive force on the fastener 22 along the central axis 36 increases the contact between the engaged beveled causing the recess 32 to "stick" onto the driver 20. The degree of "stick" created by the bevel angles 64, 68 of approximately 3.5° is sufficient to retain the fastener 22 on the drive tool 20 while the fastener 22 is being positioned for driving.

FIG. 7 illustrates the method of disengaging the drive tool 20 from the fastener 22 once the fastener is positioned as desired. By forcing the drive tool 20 to one side, thereby misaligning the bit axis 48 from the central axis 36, the "stick" between the beveled portions is loosened permitting the drive tool 20 to be extracted from the recessed socket 32. Generally, tipping the drive tool to one side and then gently rotating it in the direction in which the fastener 22 was driven promotes loosening of the beveled portions.

To further enhance the engagement and decrease wear on the drive tool 20, a coating of titanium nitride is applied to the bit tip 42 to increase the lubricity. Increased lubricity promotes insertion and reduces wear when engaging the drive tool 20 with the recessed socket 32 and further decreases wear when the drive tool 20 is tilted in order to remove it from engagement with the recessed socket 32.

In use, a drive tool 20 has a bit tip 42 which is shaped with a hexalobular 51 outer surface. Each bit lobe 52 of the hexalobular 51 surface is formed with a beveled portion 60 which slopes inwardly towards the bit axis 48. The fastener 22 is formed with a recessed socket 32 which has an internal hexalobular surface corresponding to the drive tool 20 hexalobular 51 surface. Three non-neighboring recess flutes 56 of the recessed socket 32 are formed with flute beveled surfaces 66 which are cooperatively sloped to engage the tool beveled surfaces 60.

To drive a fastener 22, the bit tip 42 of the drive tool 20 is inserted into the recessed socket 32 of the fastener 22. Rotational torque is imparted on the drive tool 20 thereby rotating the fastener 22 to threadedly engage it in a work surface. Engagement of the drive tool 20 and recessed socket 3 results in triangularized engagement 88 thereby preventing wobble while the fastener 22 is being drive. Further, the triangularized engagement 88 promotes self-centering of the bit axis 48 with the central axis 36 of the fastener. As well as reducing wobble and promoting self-centering, the beveled portions and triangularized engagement 88 permit the fastener 22 to be releasably retained on the drive tool 20.

Removal of the drive tool 20 from the recessed socket 32 is accomplished by tilting the drive tool 20 to slightly misalign the bit axis 48 from the central axis 36. By misaligning these axes 48, 36 and gently rolling the drive tool 20 in the direction in which the fastener 22 was driven the tool is easily removed.

While a preferred embodiment of the present invention is shown and described, it is envisioned that those skilled in the art may devise various modifications of the present invention without departing from the spirit and scope of the appended claims.

The invention is claimed as follows:

1. A threaded fastener with tool engaging means on a threaded shank adapted for use with a drive tool, said tool engaging means comprising: a recessed socket formed in an end of said shank for receiving a drive tool, said recessed socket having a top edge and a bottom edge; a central axis extending longitudinally through the fastener; alternating concave and convex partially-cylindrical surfaces formed inside said recessed socket, the axes of curvature of said partially-cylindrical surfaces being generally parallel to each other and to said central axis, said recessed socket formed with at least three concave partially-cylindrical surfaces; beveled surface portions formed on three of said concave surfaces sloping towards the central axis from the top edge of the recess to the bottom edge thereof, and said three concave surfaces being disposed generally at the apices of an equilateral triangle, said beveled portions formed for releasably engaging mating beveled surfaces formed on complementarily formed convex surfaces on said drive tool.

2. A threaded fastener with tool engaging means on a threaded shank adapted for use with a drive tool, said tool engaging means comprising: an end surface formed on an end of said fastener; a recessed socket formed in said end surface for receiving a drive tool, said recessed socket having a top edge and a bottom edge; a central axis extending through said fastener; alternating merging concave and convex curved partially-cylindrical surfaces formed inside said recessed socket, the axes of curvature of said partially-cylindrical surfaces being generally parallel to each other and to said central axis, said recessed socket formed with six concave partially-cylindrical surfaces; beveled surface portions formed on said concave partially-cylindrical surfaces sloping towards the central axis from the tope edge of the recess to the bottom edge thereof for releasably engaging complementarily beveled surface portions formed on said drive tool, said beveled surface portions formed on at least three alternately spaced concave partially-cylindrical surfaces such that each beveled surface portion neighbors at least one non-beveled concave partially-cylindrical surface.

3. A threaded fastener as in claim 2 wherein said beveled surfaces taper from a top edge of said recessed socket downwardly towards the bottom of said recessed socket.

4. A threaded fastener as in claim 2 wherein said beveled surface portions are sloped downwardly at an angle of less than 5°.

5. A threaded fastener as in claim 3 wherein said beveled surface portions taper downwardly inwardly toward said central axis at an angle of approximately 3.5°.

6. A threaded fastener with tool engaging means on a threaded shank adapted for use with a drive tool, said tool engaging means comprising: an end surface formed on an end of said fastener; a recessed socket formed in said end surface for receiving a drive tool, said recessed socket having a top edge and a bottom edge; a central axis extending longitudinally through the fastener; alternating merging concave and convex partially-cylindrical surfaces formed inside said recessed socket, the axes of curvature of said partially-cylindrical surfaces being generally parallel to each other and to said central axis, said recessed socket formed with at least five concave partially-cylindrical surfaces; beveled surface portions formed on at least three concave partially-cylindrical surfaces in said recessed socket of which at most two of said beveled surfaces are formed on neighboring concave partially-cylindrical surfaces, said beveled surface portions slope towards the central axis from the top edge of the recess to the bottom edge thereof for releasably engaging complementarily beveled surface portions formed on mating convex partially-cylindrical surfaces formed on said drive tool; said complementarily beveled surface portions being sloped inwardly towards said central axis.

7. A fastener and driver combination comprising: a threaded fastener with an end surface formed on an end of said fastener, engagement means formed on said end surface for receiving said driver, said recessed socket having a top edge and a bottom edge, a central axis extending longitudinally through said fastener; a driver for imparting rotational torque to said fastener and including a drive bit portion engagable with said engagement means, a bit axis extending longitudinally through said bit; alternating merging concave and convex partially-cylindrical surfaces formed on an outside surface of one of said engagement means and said bit, mating partially-cylindrical surfaces formed on an inside surface on the other of said engagement means and said bit, the axes of curvature of said partially-cylindrical surfaces being generally parallel to each other and to said central axis and said bit axis for releasably retaining said fastener on said driver, at least five convex partially-cylindrical surfaces formed on said outside surface and matingly engagable concave partially-cylindrical surfaces formed on said inside surface; beveled surface portions being formed on said concave partially-cylindrical surfaces of said inside surface, said beveled surface portions sloping inwardly towards said central axis at an angle from the top edge of the recess to the bottom edge thereof, said beveled surface portions being formed on at least three concave partially-cylindrical surfaces of which at most two of said beveled surface portions are formed on neighboring concave partially-cylindrical surfaces, correspondingly beveled surface portions formed on said outside surface on each convex partially-cylindrical surface.

8. A threaded fastener and driver combination, said fastener being formed with tool engaging means on a threaded shank for engagement with said driver, said tool engaging means comprising a recessed socket formed in an end of said shank for receiving a cooperatively formed portion of said driver, said recessed socket having a top edge and a bottom edge; a central axis extending longitudinally through the fastener; alternating concave and convex partially-cylindrical surfaces formed inside said recessed socket, the axes of curvature of said partially-cylindrical surfaces being generally parallel to each other and to said central axis, said recessed socket formed with at least three concave partially-cylindrical surfaces; beveled surface portions sloping towards the central axis from the top edge of the recess towards the bottom edge thereof and are formed on three of said concave surfaces being disposed generally at the apices of an equilateral triangle; said driver being formed for imparting a rotational torque to said fastener when engaged therewith and including a bit portion formed with alternating concave and convex partially-cylindrical surfaces for complementary engagement with said alternating concave and convex partially-cylindrical surfaces formed inside said recessed socket, complementary beveled surface portions formed on each of said convex surfaces of said bit portion for complementary engagement with said beveled surface portions formed on three of said concave surfaces formed in said recessed socket, when said driver is engaged with said fastener, said beveled surfaces formed on said convex partially-cylindrical surfaces releasably engaging said beveled surface portions formed on three of said concave surfaces formed inside said recessed socket.

9. A fastener and driver combination comprising: a threaded fastener with engagement means formed on said end surface for receiving said driver, a central axis extending longitudinally through said fastener; a driver for imparting rotational torque to said fastener and including a drive bit engagable with said engagement means, a bit axis extending longitudinally through said bit and being coaxial with said central axis when said bit is engaged with said engagement means; alternating merging concave and convex partially-cylindrical surfaces formed on an outside surface of one of said engagement means and said bit, corresponding partially-cylindrical surfaces formed on an inside surface on the other of said engagement means and bit, said inside surface being defined by a top edge and a bottom edge thereof, axes of curvature of said partially-cylindrical surfaces being generally parallel each other and with said central axis and said bit axis for releasably retaining said fastener on said driver, at least six convex partially-cylindrical surfaces formed on said outside surface and matably formed concave partially-cylindrical surfaces formed on said inside surface; first beveled surface portions formed at the apices of a triangle formed between three of said partially-cylindrical surfaces formed on said inside surface, said first beveled surface portions being sloped inwardly towards said central axis from said top edge towards said bottom edge, second beveled surface portions cooperatively formed on each of said convex surfaces formed on said outside surface for engagement with said first beveled surface, when said bit is releasably inserted into said engagement means said bit is triangularly releasably engaged in said engagement means to prevent said fastener from wobbling when driven by said driver.

10. A threaded fastener as in claim 9 wherein said beveled surface portions taper inwardly toward said central axis at an angle of approximately 3.5°.

11. A fastener and driver combination according to claim 9 wherein said bit axis and said central axis are coincident.

12. A fastener and driver combination comprising: a threaded fastener with a recessed socket formed in an end surface thereof for receiving said driver, a central axis extending longitudinally through said fastener, alternating merging concave and convex partially-cylindrical surfaces formed inside said recessed socket, the axes of curvature of said partially-cylindrical surfaces being generally parallel each other and with said central axis, said recessed socket being formed with six concave partially-cylindrical surfaces; a driver for imparting rotational torque to said fastener and including a drive bit, a bit axis extending longitudinally through said bit, alternating merging concave and convex partially-cylindrical surfaces formed on an outside surface of said bit cooperatively formed to engage said partially-cylindrical surfaces formed inside said recessed socket; first beveled surface portions formed on three alternately spaced concave partially-cylindrical surfaces formed in said recessed socket, said first beveled surface portions sloped inwardly towards said central axis, cooperatively formed second bevel portions surfaces formed on each of the convex partially-cylindrical surfaces of said bit for engaging said first beveled surface portions when said bit is engaged with said recessed socket.

* * * * *